(12) United States Patent
McDaniels

(10) Patent No.: US 6,589,543 B1
(45) Date of Patent: Jul. 8, 2003

(54) HERBAL OINTMENT

(76) Inventor: Lillie M. McDaniels, 19965 Ardmore St., Detroit, MI (US) 48235

( * ) Notice: Subject to any disclaimer, the term of this patent is extended or adjusted under 35 U.S.C. 154(b) by 0 days.

(21) Appl. No.: 10/193,336

(22) Filed: Jul. 12, 2002

(51) Int. Cl.$^7$ ............... A61K 6/00; A61K 7/00; A61K 9/00
(52) U.S. Cl. ............ 424/401; 424/400; 424/825
(58) Field of Search ............... 424/401, 400; 514/825, 969

(56) References Cited

FOREIGN PATENT DOCUMENTS

ZA 9204061 A * 2/1993

* cited by examiner

Primary Examiner—Carlos A. Alpuru
Assistant Examiner—S. Howard

(57) ABSTRACT

A HERBAL OINTMENT for soothing aches and pains includes a mixture of clove oil, ginger oil, wintergreen oil, peppermint oil, ginger root powder, cayenne powder and petroleum jelly.

3 Claims, No Drawings

HERBAL OINTMENT

BACKGROUND OF THE INVENTION

1. Field of the Invention

The present invention relates to ointments and more particularly pertains to a new herbal ointment locator for treatment of external aches and pains.

2. Description of the Prior Art

The use of herbal remedies and ointments for pain relief is known in the prior art. U.S. Pat. No. 6,280,751 describes an oil composition having medicinal uses. Another type of pain reliever is U.S. Pat. No. 6,197,823 which includes a composition for reducing pain.

While these devices fulfill their respective, particular objectives and requirements, the need remains for an ointment which is economical to make and includes all natural products while delivering pain relief.

SUMMARY OF THE INVENTION

The present invention meets the needs presented above by including only organic/natural ingredients while providing pain relief.

Still yet another object of the present invention is to provide a new ointment that is topically applied to relieve pain from arthritis, backaches, headaches, inflammation of joints, stiffness, sinus headaches and other ailments.

To this end, the present invention generally comprises a mixture of clove oil, ginger oil, wintergreen oil, peppermint oil, ginger root powder, cayenne powder and petroleum jelly.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

DESCRIPTION OF THE PREFERRED EMBODIMENT

The HERBAL OINTMENT generally comprises the mixing together of the following components:

about 18 ounces of clove oil;

about 14 ounces of ginger oil;

about 28 ounces of wintergreen oil;

about 28 ounces of peppermint oil;

about 8 ounces of ginger root powder;

about 8 ounces of cayenne powder; and about 468 ounces of petroleum jelly.

The components, when mixed together, form a mixture which is ideally poured into substantially air-tight containers. The containers may be glass or plastic containers with lids for sealing such.

In use, mixture defined a topical ointment which is rubbed over the area of pain. The mixture soothes and/or removes the pain from the afflicted area.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An herbal ointment mixture, said mixture comprising clove oil, ginger oil, wintergreen oil, peppermint oil, ginger root powder, cayenne powder and petroleum jelly, wherein said petroleum jelly comprises about 81.8% of said mixture, said clove oil comprises about 3.2% of said mixture, said ginger oil comprises about 2.4% of said mixture, said wintergreen oil comprises about 4.9% of said mixture, said peppermint oil comprises about 4.9% of said mixture, said cayenne powder comprises about 1.4% of said mixture, and said ginger root powder comprises about 1.4% of said mixture.

2. An herbal ointment mixture, said mixture comprising:

about 18 ounces of clove oil;

about 14 ounces of ginger oil;

about 28 ounces of wintergreen oil;

about 28 ounces of peppermint oil;

about 8 ounces of ginger root powder;

about 8 ounces of cayenne powder; and about 468 ounces of petroleum jelly.

3. A method of making an herbal ointment mixture comprising the steps of mixing together about 14 ounces of ginger oil, about 28 ounces of wintergreen oil, about 28 ounces of peppermint oil, about 8 ounces of ginger root powder, about 8 ounces of cayenne powder, and about 468 ounces of petroleum jelly to form a mixture and pouring said mixture into a plurality of substantially air-tight containers.

* * * * *